(12) United States Patent
Mor

(10) Patent No.: US 10,677,792 B2
(45) Date of Patent: Jun. 9, 2020

(54) SYSTEM FOR DETECTION OF AN ANALYTE IN A FLUID

(71) Applicant: Gideon Mor, Ramat Gan (IL)

(72) Inventor: Gideon Mor, Ramat Gan (IL)

(73) Assignee: Gideon Mor, Ramat Gan (IL)

( * ) Notice: Subject to any disclaimer, the term of this patent is extended or adjusted under 35 U.S.C. 154(b) by 33 days.

(21) Appl. No.: 16/116,920

(22) Filed: Aug. 30, 2018

(65) Prior Publication Data
US 2020/0025758 A1    Jan. 23, 2020

Related U.S. Application Data

(63) Continuation-in-part of application No. PCT/IL2017/051151, filed on Oct. 19, 2017.

(30) Foreign Application Priority Data

Oct. 20, 2016    (GB) .................................. 1617791.7

(51) Int. Cl.
*G01N 33/543*    (2006.01)
*C12Q 1/54*    (2006.01)

(52) U.S. Cl.
CPC ......... *G01N 33/54386* (2013.01); *C12Q 1/54* (2013.01)

(58) Field of Classification Search
None
See application file for complete search history.

(56) References Cited

U.S. PATENT DOCUMENTS

| | | |
|---|---|---|
| 5,172,693 A | 12/1992 | Doody |
| 5,361,759 A | 11/1994 | Genevier et al. |
| 5,514,598 A | 5/1996 | Doody |
| 5,713,351 A | 2/1998 | Billings et al. |
| 6,044,284 A | 3/2000 | Eisenfeld et al. |
| 6,180,395 B1 | 1/2001 | Skiffington et al. |
| 2003/0228681 A1 | 12/2003 | Ritts et al. |
| 2003/0231983 A1 | 12/2003 | Schleifer |
| 2008/0056946 A1 | 3/2008 | Ahmad |
| 2010/0324391 A1 | 12/2010 | Kostenich et al. |
| 2012/0301546 A1 | 11/2012 | Hassan |
| 2013/0137188 A1 | 5/2013 | Paper et al. |
| 2013/0165816 A1* | 6/2013 | Mor ............. A61F 13/505 600/582 |
| 2015/0346212 A1 | 12/2015 | Mor |

FOREIGN PATENT DOCUMENTS

WO    WO02097398    12/2002

* cited by examiner

*Primary Examiner* — Rebecca L Martinez

(57) ABSTRACT

The invention provides a system for detection of at least one analyte present in a fluid, the system comprising a detector comprising an assay configured to detect presence of the analyte in the fluid, the detector comprising a specimen sampling region for the fluid and a protective seal partially covering the detector, wherein only the specimen sampling region is uncovered by the fluid-protective seal, and wherein the fluid-protective seal provides resistance to acid. The system can be fully submerged in an acidic solution and still retain is functionality.

27 Claims, 7 Drawing Sheets

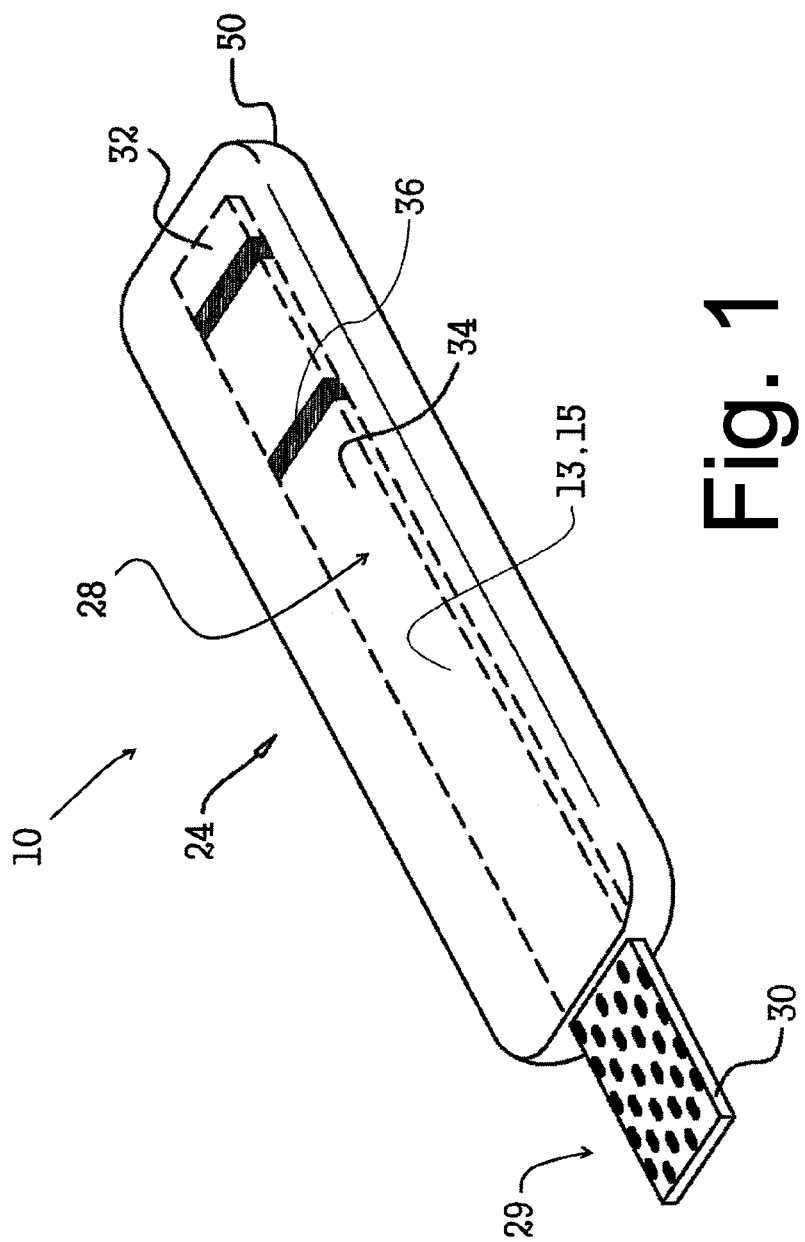

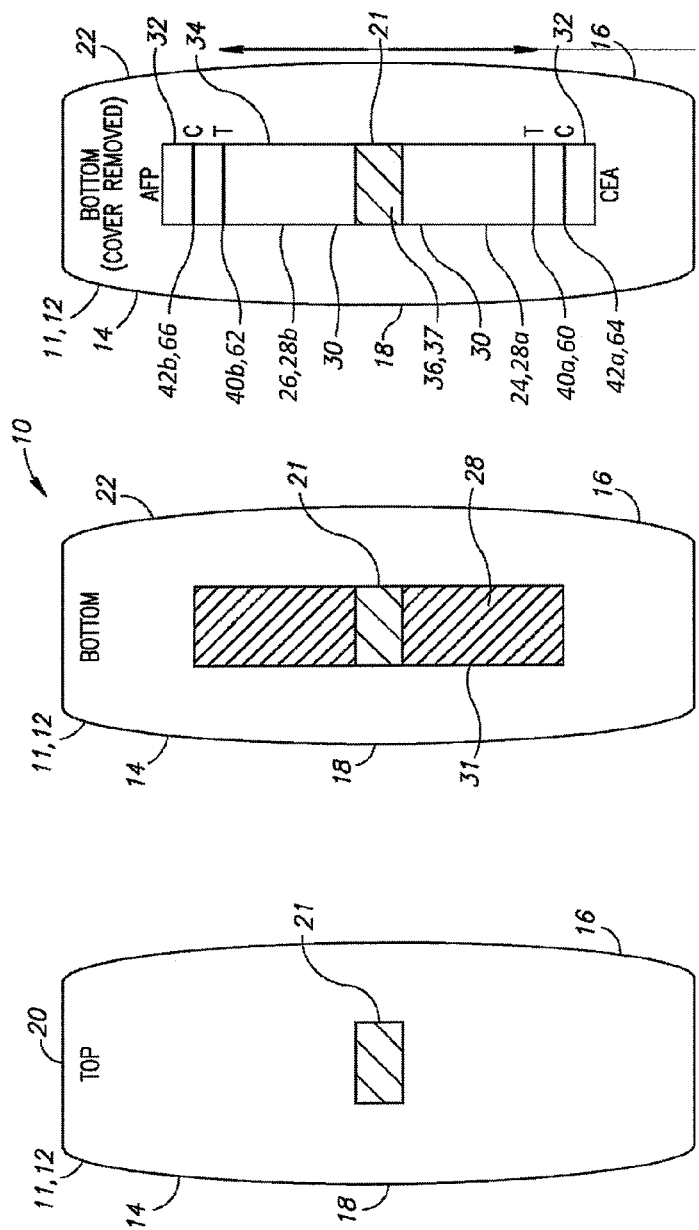

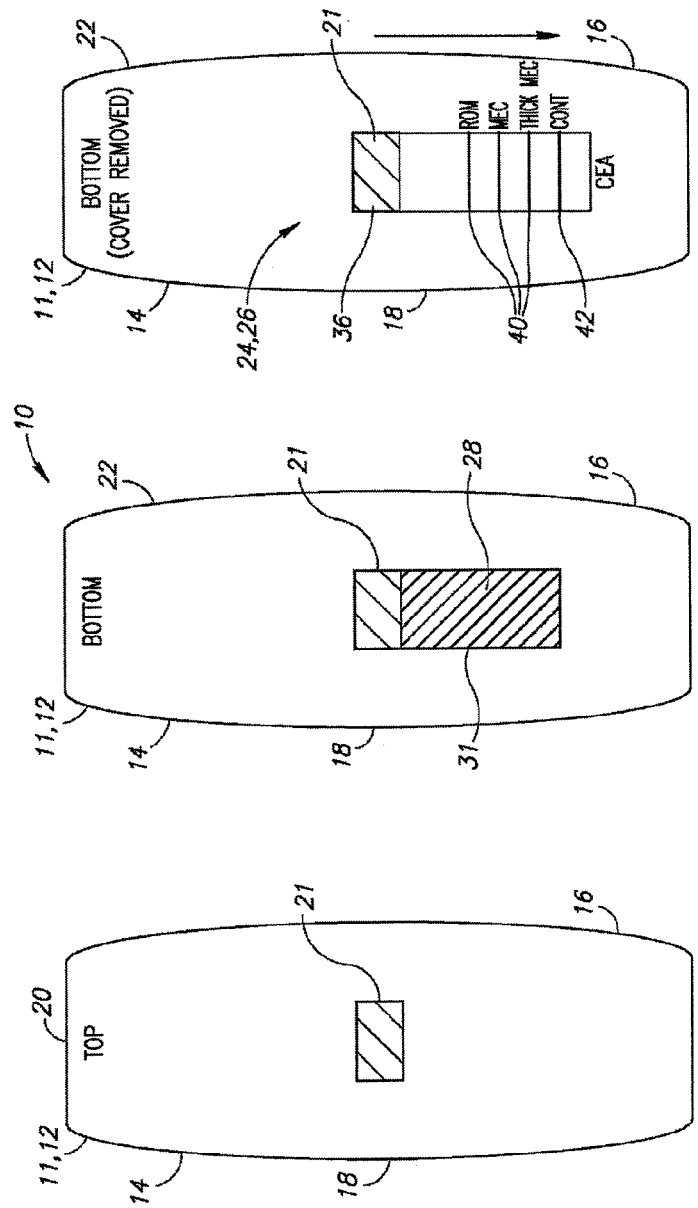

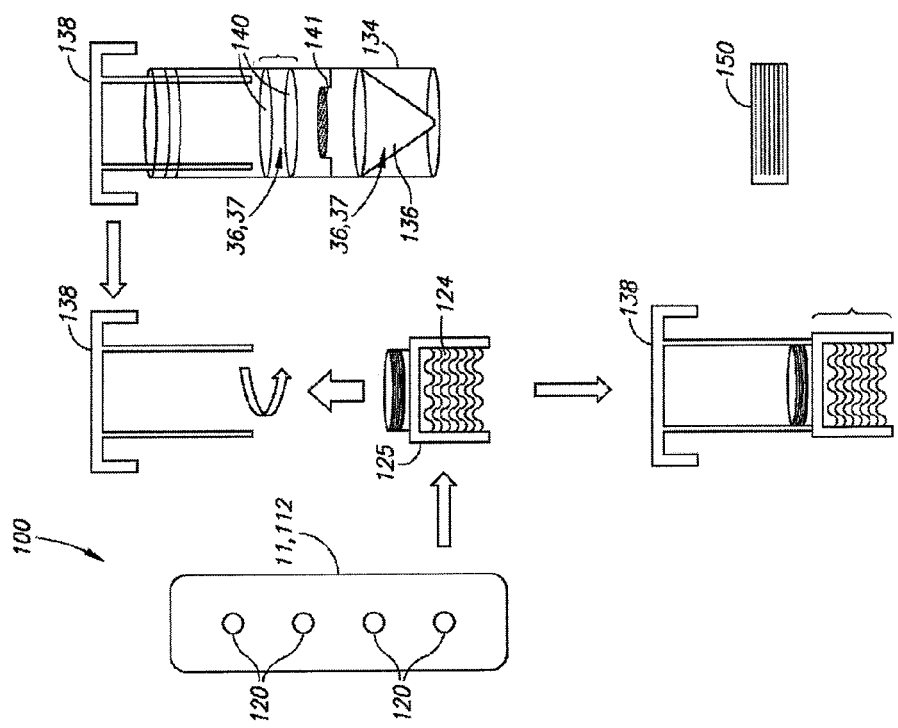

SYSTEM FOR DETECTION OF AN ANALYTE IN A FLUID

FIELD OF THE INVENTION

The present invention relates to the field of analyte detection, and more specifically to an analyte detection system which is at least partially covered with a fluid-protective seal providing improved resistance to damage by acid.

BACKGROUND OF THE INVENTION

An immunoassay is a biochemical test that measures the presence or concentration of a macromolecule or a small molecule in a solution, based on the ability of an antibody to recognize and bind a specific antigen, wherein a measurable signal is produced upon binding.

The molecule detected by the immunoassay is referred to as an "analyte" and is generally a protein.

Immunoassays may be used for detection of an analyte in a biological fluid e.g. blood or urine, or in a non-biological fluid e.g. drinking water.

Most immunoassays for detection of an analyte in a biological fluid must be employed by medical personnel, often requiring the use of additional equipment, such that testing must be carried out at medical facilities.

An example of an analyte which may be detected in a biological fluid is meconium. The colon of a fetus during gestation fills with meconium, the fetal feces comprising bile and its metabolites, gastrointestinal and pancreatic secretions, mucus, cellular debris, swallowed vernix caseosa, and blood. In a significant minority of births, the fetus ceases to be continent and excretes meconium into the amniotic fluid. It is important to be aware of such an occurrence for the future mother and for the obstetrics personnel.

The fetus may pass stool to the amniotic fluid in response to stress (e.g., hypoxemia) and then inhale it into the lungs. Fetal stool, meconium, is toxic in the lungs, it can obstruct airways, and also does harm by other mechanisms, resulting in meconium aspiration syndrome (MAS). Meconium aspiration may occur before, during, and after labor. About 13% of all live births are complicated by meconium-stained amniotic fluid (MSAF), and about 30,000 develop MAS annually in the United States, leading to the death of 1000 children. MSAF is associated with an increased risk for perinatal complications during labor and delivery (e.g., low Apgar score, higher risk for cesarean section, and higher admission rate to neonatal intensive care unit. MSAF is considered to be a marker for possible fetal compromise. Prenatal detection of meconium in the amniotic fluid can alert a caregiver or patient to intrauterine fetal distress and might have an important role in reducing the incidence and consequences of MAS, fetal hypoxemia, and cerebral palsy. Moreover, when meconium concentration is high—designated herein as thick meconium, the amniotic fluid has a dark green opaque color. Heavy (thick) MSAF may indicate worse fetal/neonatal prognosis than light (thin) MSAF.

There is a consensus that a pregnant woman with MSAF should be carefully evaluated for fetal well-being in order to reduce the chances of irreversible damage to the fetus/newborn. To date, a number of invasive and non-invasive methods and devices are known to identify MSAF. Amniocentesis is an invasive sampling procedure removing a small volume of the amniotic liquid for in vitro testing. U.S. Pat. No. 5,361,759 describes an invasive method for detection of undesired components, including meconium, in amniotic fluid by absorbance spectroscopy of a sample of amniotic fluid acquired by penetrating the amniotic sac. U.S. Pat. No. 5,713,351 describes an invasive method for the detection of meconium in amniotic fluid by penetrating the amniotic sac with a probe and withdrawing amniotic fluid through the lumen of the probe into an observation chamber. Amnioscopy is a less invasive technique, enabling direct observation of the forebag of an amniotic sac to look for meconium staining; it may help in detecting heavy staining by meconium, but milder cases remain undetected, and the method may require an undesirable degree of cervical dilation. U.S. Pat. No. 5,172,693 describes the detection of meconium in the amniotic sac by detecting fluorescence of the bilirubin component of meconium, placing a probe against the uterine wall and irradiating the amniotic fluid through the body tissues by excitation light, leading to characteristic fluorescence of eventual meconium components in vivo. US 2010/0324391 describes a device for detecting meconium in amniotic fluid by fluorescent measurement of zinc coproforphyrin in vivo. U.S. Pat. No. 6,044,284 relates to an apparatus for measuring the concentration of meconium in amniotic fluid by employing optical sensors measuring the fluid transmittance in vivo. The above approaches are characterized by physical or optical penetration into the amniotic sac. U.S. Pat. No. 5,514,598 describes a non-invasive method to detect MSAF: a specific meconium protein (14 kilodaltons) can be detected by immunological techniques.

All approaches described above must be employed by professional personnel and, therefore, limit their use to medical facilities. As a matter of fact, high quality fetal wellbeing monitoring is still restricted to skilled personnel (e.g., ultrasonographic fetal heart rate tracing, biophysical profiling, and amniotic fluid indexing).

Rupture of the amniotic sac membranes may occur throughout almost the whole pregnancy period. When rupture of membranes (ROM) occurs, umbilical cord (UC) prolapse (0.5 percent of all pregnancies) can be one of the biggest threats to the fetus. UC prolapse occurs when a UC loop precedes the leading part of the fetus (during spillage of amniotic fluid from the uterine cavity). During this process the UC loop may be compressed and result in imminent fetal asphyxia. In a significant minority of term pregnancies (37-40 gestational weeks) 10-15% of women arrive at the hospital with their 'water already broken'. ROM and the associated severe complications (e.g., UC compression, placental abruption) may occur at home, away from a medical facility. Failure to recognize and immediately treat these complications may result in fetal death. A well-established possible indicator for these complications is MSAF.

To date, there is no simple accurate method or device that enables home detection of MSAF by lay people. Furthermore, nowadays MSAF can be detected at home by the naked eye only. However, in a significant number of events MSAF may be bloody or may be lightly stained and therefore not detectable by the naked eye. Another important aspect is the ability to identify the etiology for MSAF (and the possible fetal distress) at home by lay people, as well as the potential severity of the MSAF. To date, there is no simple method or device enabling such a thing. It is an object of this invention to enable the detection of MSAF by lay personnel.

Thus, there is a need for: a) Providing a method of detecting MSAF without penetration into the amniotic sac; b) Providing a sensitive and specific method and kit for detecting MSAF (including bloody or lightly stained MSAF) without employing complex analytical tools or devices; c) Providing a method and a kit for detecting MSAF that can be employed by unskilled users at home; d) Providing a platform for identifying etiologies for fetal distress after ROM has occurred; e) Providing an inexpensive home kit that will reduce medical costs by early identification of fetal distress; and (f) Providing a method and kit for differentiating between thick and thin MSAF.

An immunoassay system for home use by non-skilled personnel for detection of meconium in amniotic fluid is described in US20150346212A1 to the present inventor. However, it has been found that such an immunoassay system may be susceptible to damage during use. For example, the integrity of the seal may be breached or the transparency of the seal may be lost during use.

There is a need for an improved immunoassay system for detection of at least one analyte in a biological or non-biological fluid, which is suitable for use by unskilled personnel, which is reliable, durable and damage-resistant during storage and use.

SUMMARY OF THE INVENTION

The invention, in some embodiments thereof, relates to an analyte detection system including a detector which is at least partially covered with a fluid-protective seal providing improved resistance to damage by acid.

The analyte detection system is useful for detection of analytes in biological or non-biological fluids.

Aspects and embodiments of the invention are described in the specification hereinbelow and in the appended claims.

In some embodiments, the system of the present invention is useful for detection of meconium in amniotic fluid. After rupture of membranes (ROM) occurs there may be a prolonged amniotic fluid outflow. The fluid may be "meconium free" initially, and later on become meconium-stained amniotic fluid (MSAF).

Some embodiments of the present invention provide the ability to detect the presence of normal amniotic fluid and to detect when and if it changes to MSAF. The ability to detect actual meconium secretion provides real time information on possible ongoing fetal distress. The knowledge that clear amniotic fluid becomes MSAF may significantly affect the medical management.

In some instances, an event of "water break" at home can be massive and become a transient, one-time event. In this case, when the pregnant woman arrives at a medical center, the physician may fail to detect any fluid coming out of the cervical canal/vagina. Under these circumstances MSAF can be missed, and different (or wrong) medical management will ensue. Some embodiments of the present invention provide the ability to "catch" a transient, one-time event of MSAF secretion at home.

Artificial ROM for labor induction (employed by medical personnel) may expose the presence of MSAF. However, frequently MSAF is mixed with blood, mucus, and vernix, which make its detection difficult (even by professional experienced personnel). Some embodiments of the present invention provide a sensitive method and kit that enables bedside detection of MSAF even when it is mixed with other substances.

U.S. Patent Publication No. 2010/0324391 and others describe a device for detecting MSAF inside an intact sac before ROM. Some embodiments of the present invention may provide a complementary solution, which may serve as a complete approach for MSAF detection before and after ROM, and until birth.

Some embodiments of the present invention may provide a platform of etiology(ies) for fetal distress. For example, uncontrolled Diabetes Mellitus (gestational, type 1, or type 2) is one of the leading causes of intrauterine fetal death during the third trimester. Information on the amniotic fluid sugar level may help with the assessment and the emergent management of the diabetic pregnant woman with MSAF. High amniotic fluid sugar level may point to the cause for MSAF and fetal distress. Other life-threatening events may comprise significant maternal or fetal bleeding. Another example is ROM resulting in meconium-free amniotic fluid outflow, stained with maternal blood (a normal condition), followed by MSAF with fetal blood (a condition indicating placental abruption and fetal asphyxia). This change is not detected by the naked eye. Generally speaking, the use of bedside colorimetric reactions for glucose, fetal hemoglobin, fetal tissue, fetal proteins, maternal proteins, DNA, RNA, etc., provides an added value of early detection of several pathophysiological conditions. In this way, critical time can be saved upon arriving at the appropriate medical center.

It is known in the field of immunoassay systems to provide a detector which is at least partially covered with a fluid-protective seal, the seal preferably comprising a hydrophobic material such as nylon or polyester, to enable the system to be immersed in a fluid without the fluid gaining access to portions of the system other than the sampling region.

However, it has been found that such fluid-protective seals are often susceptible to damage during use. It has surprisingly been found that damage to a nylon or polyester seal is frequently caused by prolonged exposure to even mildly acidic conditions. For example, an immunoassay system such as that described in US20150346212A1 to the present inventor, for detection of amniotic fluid, and which may comprise a nylon or polyester seal, is intended to be positioned in proximity to the vaginal opening of a pregnant woman, such as in a panty. In such a case, the material of the seal may be subjected to prolonged contact with body fluids having acidic pH (generally in the region of from about 3.5 to about 6), such as urine or vaginal excretion. Such exposure may cause damage to the outer surface of the fluid-protective seal, destroying its integrity and/or its transparency. In particular, the urine may become more acidic in a subject suffering from uncontrolled diabetes (including gestational diabetes), reaching pH values as low as 3.5. This is exacerbated by the fact that urine incontinence is a very common occurrence during pregnancy, due to the pressure of the growing uterus on the bladder, such that over a prolonged period of use, the material of seal may be subjected to a significant amount of contact with acidic urine.

Furthermore, even in non-pregnant women, the normal pH of the vagina is about 3.5-4.5, such that discharge from the vagina is normally acidic.

In cases wherein an immunoassay system is used for detection of an analyte within a non-biological fluid, such as a body of water, e.g. seawater, the system may be exposed to acid present in the water, causing damage to the integrity and/or transparency of the outer surface of the seal.

The present inventor hypothesizes that acids attack the covalent bonds in nylon and polyester and thereby breach the integrity of a fluid-protective seal made from these materials.

The present inventor has surprisingly found that covering a detector of an assay system with a seal comprising a material having improved acid resistance, such that all outer surfaces of the detector other than the specimen sampling region are covered by the seal, improves accuracy and stability of the assay system.

In embodiments in which the detector is an immunoassay strip, the seal is thus positioned over the entirety of the outer surfaces of the body and back tip of the detector, with the exception of the front tip, comprising specimen sampling region, which is left uncovered by the seal in order to allow entry of test fluid into the detector.

According to some embodiments, the seal is positioned directly on the outer surfaces of the body of the detector.

In embodiments in which the detector is an immunoassay strip, the seal is thus positioned over the entirety of the outer surfaces of the body portion and back tip of the detector, with the exception of the front tip, comprising the specimen sampling region, which is left uncovered by the seal in order to allow entry of test fluid into the detector.

In embodiments wherein the detector comprises an immunoassay strip, the use of such a seal was found to increase accuracy and stability of the immunoassay system, without interfering with or slowing down the capillary action along the immunoassay strip.

According to an aspect of some embodiments of the present invention, there is provided a system for detection of at least one analyte present in a fluid, the system comprising:
  a detector configured to detect presence of the at least one analyte in the fluid, the detector comprising a specimen sampling region for the fluid; and
  a fluid-protective seal positioned over a portion of the detector, such that only the specimen sampling region is uncovered by the fluid-protective seal,
  wherein the fluid-protective seal comprises a material having acid resistance to an acid solution of pH 3.5 to 6, Acid resistance to the acid solution of pH 3.5 to 6 comprises at least one property selected from the group consisting of resistance to loss of transparency for at least 30 seconds upon full immersion in the acid solution of pH 3.5 to 6; resistance to passage of fluid for at least 30 seconds upon full immersion in the acid solution of pH 3.5 to 6; and retention of physical integrity for at least 30 seconds upon full immersion in the acid solution of pH 3.5 to 6. In the context of the present invention, a fluid-protective seal is considered to have "resistance to loss of transparency" up to the point at which two parallel, solid, black lines, printed on a white paper sheet, the lines having length of 10 mm long, thickness of 1 mm, and separation distance of 2 mm, cannot be distinguished one from the other by the normal human eye.

In the context of the present invention, a fluid-protective seal is considered to have "resistance to passage of fluid" up to the point at which a first drop of a liquid can be seen to pass through the seal by the normal human eye.

In the context of the present invention, a fluid-protective seal is considered to retain physical integrity up to the point at which a first break, crack or lesion can be seen by the normal human eye.

In some embodiments, the fluid-protective seal is stable in urine in the normal physiological pH range of from about 4.5 to about 8. The fluid-protective seal may comprise, for example, polyethylene or flexible glass.

The present inventor has further found that visualisation of the result of a chromotagraphic assay is often difficult when the fluid in which an analyte is to be detected is a body fluid which comprises red blood cells. Hence, in some embodiments of the system of the present invention, the specimen sampling region is configured to bind platelets within 50 seconds.

In some such embodiments, the specimen sampling region comprises a material selected from the group consisting of oxidized cellulose, absorbent material with glass fragments and absorbent material with kaolin.

In some embodiments wherein the system of the present invention comprises an immunoassay, the immunoassay comprises a lateral flow immunochromatographic assay.

In some embodiments wherein the system of the present invention comprises an immunoassay, the immunoassay comprises an immunoassay strip. In some such embodiments, the immunoassay strip comprises a front tip, a back tip, an upper body portion and a lower body portion extending between the front tip and the back tip, wherein the specimen sampling region comprises the front tip of the strip, each of the front tip, back tip, upper body portion and lower body portion comprising an outer surface, wherein the fluid-protective seal is positioned on the outer surfaces of the upper body portion, lower body portion and back tip, such that only the front tip is uncovered by the fluid protective seal, such that the fluid comes into contact with the front tip and is carried along the strip body to the back tip. In some embodiments, wherein the system of the present invention comprises an immunoassay strip, the immunoassay strip comprises a first antibody for reacting with at least one analyte of the fluid, wherein the antibody is positioned at the front tip of the strip.

It should be noted that the detector of the present invention is not limited in shape to the form of a strip. In some embodiments, the detector may comprise any shape having a front and a back tip. Alternatively, in some embodiments, the detector may be provided in the form of a shape which does not have a front and back tip, such as, for example, in the form of a spiral or circle. In embodiments which do not have a front and back tip, the fluid sampling region may be positioned at any suitable location on or within the body portion of the detector, provided that the position enables the outer surface of the body portion of the detector to be covered by the fluid protective while allowing the specimen sampling region to remain uncovered by the seal. Hence, in such embodiments, the fluid protective seal is positioned over each outer surface of the body portion of the detector (such as the outer surfaces of the upper and lower body portions), such that the specimen sampling region is not covered by the seal.

In the context of the present invention, the term "body portion" of the detector is intended to mean the portion of the detector within which flow of fluid from the specimen sampling region occurs and within which the detection process is carried out.

As used herein, the term "detector" refers to a physical device configured to detect the presence of an analyte in a fluid.

In some embodiments, the system further comprises a fluid identifier comprising a reagent for reacting with the fluid, wherein the reagent is configured to identify the fluid.

In some embodiments, the fluid comprises a body fluid released from the body of a subject, such as, for example, amniotic fluid, urine, saliva, sweat, vaginal discharge, semen or blood.

In some embodiments, the body fluid is amniotic fluid and the detector comprises a detector for the presence of at least one analyte of amniotic fluid selected from the group consisting of a carbohydrate and a protein (such as, for example, alpha-fetoprotein (AFP), carcino-embryonic antigen (CEA), epithelium carcinoma associated Antigen (SCCA), placental alpha-microglobulin-1 (PAMG-1), CA-125 tumor marker, Insulin-like growth factor binding protein-1 (IGFBP-1), Prostate serum antigen (PSA) or diamine oxidase).

In some embodiments, the protein comprises AFP, and the detector for presence of AFP is configured to detect an amount of AFP in a sample of body fluid, wherein a presence of amniotic fluid is indicated when the detected amount of AFP is above a pre-determined threshold, such as, for example, above approximately 10 ng/ml.

In some embodiments, the protein comprises CEA, and the detector for presence of CEA is configured to detect an amount of CEA in a sample of body fluid, wherein a presence of amniotic fluid is indicated when the detected amount of CEA is above a pre-determined threshold, such as, for example, above at least 5 ng/ml.

In some embodiments, the system further comprises a collection body for collecting a body fluid. In some such embodiments, the collection body comprises at least a portion of a hygienic pad, a panty, a tampon, or an applicator.

In some embodiments, the fluid comprises a non-body fluid, such as, for example, a liquid selected from the group consisting of sea water, rainwater, river water, lake water, reservoir water, well water, a source of drinking water, and sewage.

In some embodiments, the detector comprises a detector for the presence of an analyte selected from the group consisting of 2,4,6-trinitrotoluene, asbestos, benzene, aflatoxins, ricin, cholera toxin, prion, pertussis toxin, ectatomin, conopeptides, abrin, verotoxin, tetanospasmin, botulinum toxin, DNA and RNA (including DNA or RNA from human and non-human animal, viral, or bacterial sources).

In some embodiments, the detector is located externally to the collection body.

In some embodiments, at least a portion of the collection body is detachable, wherein the detector is configured to detect presence of the at least one analyte in the fluid collected in the detachable portion of the collection body.

In some embodiments, there is provided a kit for detection of at least one analyte present in a fluid, the kit comprising: at least one detector configured to detect presence of the at least one analyte in the fluid, the at least one detector comprising a specimen sampling region for the fluid and a fluid-protective seal positioned over a portion of the at least one detector, such that only the specimen sampling region is uncovered by the fluid-protective seal, wherein the fluid-protective seal comprises a material having acid resistance; and at least one collection body for collecting the fluid.

In some embodiments of the kit, the detector comprises an immunoassay. In some embodiments, the kit further comprises printed instructions for use, such as a guide booklet, insert or instruction manual.

In some embodiments, there is provided a method of detecting at least one analyte present in a fluid, the method comprising:
  providing a system for detection of at least one analyte present in a fluid, the system comprising a detector configured to detect presence of the at least one analyte in the fluid, the detector comprising a specimen sampling region for the fluid and a fluid-protective seal positioned over a portion of the detector, such that only the specimen sampling region is uncovered by the fluid-protective seal, wherein the fluid-protective seal comprises a material having acid resistance;
  collecting the fluid; and
  contacting the fluid with the detector.

In some embodiments of the method, the detector comprises an immunoassay.

In some embodiments of the method, the detector comprises a colorimetric reaction for the detection of RNA, DNA, or small analytes that can not bind antibodies. In such detection reactions the biorecognition molecules can be aptamers or molecular beacons rather of antibodies.

Unless otherwise defined, all technical and scientific terms used herein have the same meaning as commonly understood by one of ordinary skill in the art to which this invention belongs. Although methods and materials similar or equivalent to those described herein can be used in the practice or testing of the embodiments of the present invention, suitable methods and materials are described below. In case of conflict, the patent specification, including definitions, will control. In addition, the materials, methods, and examples are illustrative only and not intended to be limiting.

Unless otherwise defined, all technical and scientific terms used herein have the same meaning as commonly understood by one of ordinary skill in the art to which the invention pertains. In case of conflict, the specification, including definitions, takes precedence.

As used herein, the terms "comprising", "including", "having" and grammatical variants thereof are to be taken as specifying the stated features, integers, steps or components but do not preclude the addition of one or more additional features, integers, steps, components or groups thereof.

As used herein, the indefinite articles "a" and "an" mean "at least one" or "one or more" unless the context clearly dictates otherwise.

As used herein, when a numerical value is preceded by the term "about", the term "about" is intended to indicate +/−10%.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of various embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several embodiments of the invention may be embodied in practice.

In the drawings:

FIG. 1 is a schematic illustration of a system for detection of an analyte in accordance with one embodiment of the present invention;

FIGS. 2A, 2B, 2C are schematic illustrations of the system of FIG. 1 provided within a hygienic pad;

FIGS. 3A, 3B, 3C are schematic illustrations of a hygienic pad for prenatal detection of meconium including a lateral flow immunochromatographic assay in accordance with another embodiment of the present invention;

FIGS. 4A and 4B are schematic illustrations of a kit for prenatal detection of meconium according to one embodiment of the invention, the kit comprising a multi-patch hygienic pad with detachable collection members, and a reaction bottle;

Figure 4B:
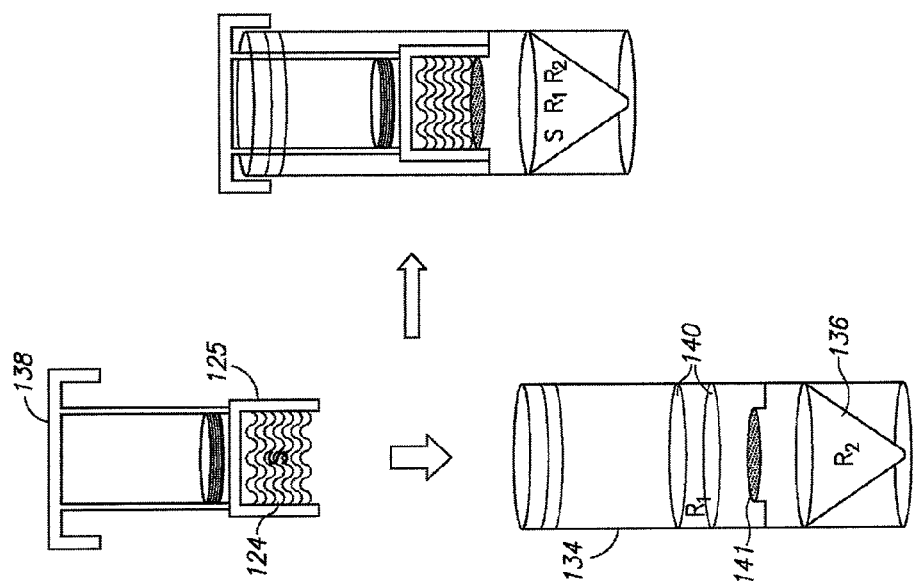

It will be appreciated that for simplicity and clarity of illustration, elements shown in the drawings have not necessarily been drawn accurately or to scale. For example, the dimensions of some of the elements may be exaggerated relative to other elements for clarity or several physical components may be included in one functional block or element. Further, where considered appropriate, reference numerals may be repeated among the drawings to indicate corresponding or analogous elements. Moreover, some of the blocks depicted in the drawings may be combined into a single function.

DETAILED DESCRIPTION OF THE INVENTION

The present invention, in at least some embodiments thereof, relates to an analyte detection system including a detector which is at least partially covered with a fluid-protective seal providing improved resistance to damage by acid.

Referring now to FIG. 1, there is shown a system 10 for detection of at least one analyte present in a fluid. System 10 comprises a detector 24 configured to detect presence of the analyte in the fluid. Detector 24 comprises a specimen sampling region 29 for the fluid. Detector 24 is partially covered by a fluid-protective seal 50, such that only specimen sampling region 29 is uncovered by fluid-protective seal 50. Fluid-protective seal 50 comprises a material having acid resistance, such as, for example, polyethylene or flexible glass.

According to some embodiments, the acid resistant material provides resistance to an acid solution in the pH range of from about 3.5 to about 6, such that the seal exhibits one or more of retention of transparency, resistance to passage of fluid, or retention of physical integrity upon full immersion for at least 30 seconds in an acid solution of pH from about 3.5 to about 6. In some embodiments, the seal exhibits acid resistance upon full immersion in the acid solution for about 30 seconds, about 40 seconds, about 50 seconds, about 60 seconds, about 2 minutes, about 3 minutes, about 4 minutes, about 5 minutes, about 10 minutes, about 15 minutes, about 15 minutes, about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, or even about 24 hours. In some embodiments, fluid-protective seal 50 is transparent.

In some embodiments, detector 24 comprises an immunoassay 13 or a lateral flow assay 15. In some embodiments, detector 24 is a lateral flow immunochromatographic assay. In some such embodiments, as shown in FIG. 1, detector 24 is a strip 28, such as a lateral flow immunochromatography assay strip used for detection of components such as proteins and glycoproteins. Such assay strips are known in the art and may be obtained from, for example, CEA Serum Rapid Test (Strip 5 mm) RapiDip™ Instatest (Diagnostic Automation/Cortez Diagnostics, Inc., California, USA).

It should be noted that for illustrative purposes, fluid-protective seal 50 has been shown in FIG. 1 as having considerable thickness relative to the thickness of strip 28. Fluid-protective seal 50 preferably has a thickness in the range of from about 0.002 micron to about 3 mm, more preferably about 50 micron.

It should be readily apparent that strip 28 is not limited to the type disclosed herein, and that any suitable strip may be used. In the embodiment shown herein, strip 28 (an exemplary embodiment of detector 24) has a front tip 30 and a back tip 32, with a body portion 34 extending from front tip 30 to back tip 32. In such embodiments, front tip 30 comprises specimen sampling region 29. Strip 28 acts by capillary action, wherein fluid comes into contact with front tip 30, and is carried along body portion 34 to back tip 32. Body portion 34 comprises at least one reagent which interacts with at least one analyte in the fluid, causing the analyte to be separated out from the fluid and identified.

In some embodiments, fluid-protective seal 50 is positioned over body portion 34 and back tip 32, while only front tip 30 is left unsealed. In some such embodiments, fluid-protective seal 50 is positioned in direct contact with body portion 34 and back tip 32 such that no gap is provided therebetween. In this way, fluid contacting specimen sampling region 29 will leak into strip 28 only via front tip 30 and will be carried through strip 28 in a single direction, from front tip 30 to back tip 32. The direction of flow may be important in ascertaining that a valid reaction occurs.

In embodiments of the present invention, strip 28 includes a first reagent 36 for reacting with at least one analyte in the fluid. First reagent 36 may be, for example, an antibody or series of antibodies, an enzyme, a color pigment, multiple color pigments, color pigments attached to antibodies, color pigments sensitive to chemical products, a DNA or RNA probe, an aptamer, a molecular beacons or any other relevant reagent.

In some embodiments of the present invention, detector 24 includes a test indicator 40 and a control indicator 42, wherein test indicator 40 is configured to positively identify the presence of at least one analyte, and wherein control indicator 42 is configured to confirm reliability of the assay (see FIG. 2C).

It is an additional feature of some embodiments of the present invention that specimen sampling region 29 comprises a material that binds platelets within 50 seconds, such that platelets and red blood cells are removed from the fluid (with or without the formation of clot), resulting in a clearer solution. In some embodiments, wherein a visual indicator of the presence of an analyte in a liquid is provided in system 10, removal of red blood cells from the liquid enables the indicator to be viewed more easily. Non-limiting examples of suitable materials include oxidized cellulose, absorbent material with glass fragments and absorbent material with kaolin. Non-limiting examples of suitable absorbent materials include paper, cotton, starch-acrylonitrile co-polymer, polyvinyl alcohol copolymers, and cross-linked polyethylene oxide.

In some embodiments, system 10 further comprises a collection body 11 for collecting a sample of a fluid to be tested.

In some embodiments, wherein the fluid is a biological fluid released from the vaginal or urethral opening of a human female, collection body 11 may be, for example, a portion of a hygienic pad, specially designed panty, a tampon, or the like. In some such embodiments, collection body 11 may comprise one or more absorbent portions 21, which are spatially defined areas for absorbing the body fluid and enabling transfer of the fluid to specimen sampling region 29 and subsequently detector 24.

In some embodiments, at least one absorbent portion 21 is impregnated with a detection solution for detecting at least one analyte present in the body fluid. In some such embodiments, detector 24 comprises the detection solution. In some such embodiments, specimen sampling region 29 and detector 24 are located within at least one absorbent portion 21. In some such embodiments, specimen sampling region 29 and detector 24 are located proximal to, and in fluid communication with, at least one absorbent region 21.

The detection solution may comprise a component which interacts with at least one analyte in the body fluid. For example, the component may comprise a chemical reagent which reacts with the analyte, an antibody, or an antisense nucleotide that binds the analyte.

In some alternative embodiments, system 10 is configured such that detection solution may be added to absorbent portion 21 after absorption of the body fluid. In some alternative embodiments, components of collection body 11 comprising the analyte are transferred to detection device 24 prior to contacting the analyte with a detection solution.

Body fluids in which the presence of an analyte may be detected using the system of the present invention include for example, amniotic fluid, urine, saliva, sweat, vaginal discharge, semen and blood.

Analytes to be detected may include typical components of vaginal fluids or undesired components associated with any problems during pregnancy, for example, leaked amniotic fluid, presence of meconium in the fluid, infection, and bleeding. In some such embodiments, detection device 24 is configured to detect leaked amniotic fluid and/or to detect meconium in amniotic fluid. In some such embodiments, detection device 24 is configured for detecting thick meconium and for differentiating between thick and thin meconium.

In some embodiments wherein the body fluid is amniotic fluid, detector 24 is configured to detect the presence of at least one analyte of amniotic fluid, such as a carbohydrate or a protein (e.g. alpha-fetoprotein (AFP), carcino-embryonic antigen (CEA), epithelium carcinoma associated Antigen (SCCA), placental alpha-microglobulin-1 (PAMG-1), CA-125 tumor marker, Insulin-like growth factor binding protein-1 (IGFBP-1), Prostate serum antigen (PSA) or diamine oxidase).

In some embodiments, wherein the protein comprises AFP, detector 24 is configured to detect an amount of AFP in a sample of body fluid. In some such embodiments, the presence of amniotic fluid is indicated when the detected amount of AFP is above a pre-determined threshold, such as, for example, above about 10 ng/ml.

In some embodiments, wherein the protein comprises CEA, detector 24 is configured to detect an amount of CEA in a sample of body fluid. In some such embodiments, the presence of amniotic fluid is indicated when the detected amount of CEA is above a pre-determined threshold, such as, for example, above about 5 ng/ml.

In some embodiments, system 10 further includes a fluid identifier 26 (as shown in FIG. 3C), configured to identify the fluid. For example, in embodiments wherein the fluid is a body fluid, the fluid identifier may be configured to identify at least one of amniotic fluid, urine, saliva, sweat, vaginal discharge, semen or blood.

Reference is now made to FIGS. 2A-2C, which are schematic illustrations of an exemplary system 10 for detecting meconium in amniotic fluid, in accordance with embodiments of the present invention. It is a feature of some embodiments of the present invention that system 10 is capable of detecting meconium-containing fluid with enough specificity and sensitivity that a pregnant woman may be directed to consult her doctor or go urgently to the hospital in order to be managed as a "meconium positive" high risk pregnancy.

In one embodiment, collection body 11 is a hygienic pad 12 having a first end 14, a second end 16 opposite first end 14, and a middle section 18 connecting first and second ends 14 and 16. Hygienic pad 12 further includes a top portion 20 and a bottom portion 22 on an opposite side of top portion 20, ie, on an underside of pad 12. FIG. 2A is an illustration of top portion 20, and FIGS. 2B and 2C are illustrations of bottom portion 22. Top portion 20 is the side of pad 12 which is configured to face the body orifice (i.e., the vagina), and collect fluid discharged therefrom. Bottom portion 22 is situated on the opposite side, to be positioned, when in use, adjacent to the inner surface of a panty, and in some embodiments adhesive thereto.

Hygienic pad 12 further includes at least one absorbent portion 21, which may be, for example, a patch or a portion of hygienic pad 12 so designated. Absorbent portion 21 is configured to absorb a body fluid. Absorbent portion 21 comprises absorbent material such as fiber-based materials (e.g. Whatman 3MM Chr paper, GE Health care Life Sciences, Piscataway, N.J., USA). Absorbent portion 21 may be positioned at or near first end 14, second end 16 or middle section 18 and may be relatively small or large depending on the preferred sample size. Absorbent portion 21 may extend through pad 12 from top portion 20 to bottom portion 22, as shown in FIGS. 2A and 2B. Hygienic pad 12 may be, for example, a panty liner. In additional embodiments, hygienic pad 12 may be incorporated into a panty or other undergarment. The structure of the pad comprises materials usual in personal panty liners, adherent shields, and hygienic pads.

In some embodiments, fluid identifier 26 is also a strip 28, and comprises a second reagent 37 for interacting with a component of the fluid, wherein second reagent 37 is configured to identify the fluid. In some embodiments, meconium detector 24 and fluid identifier 26 are comprised of two separate strips 28a, 28b, wherein a first strip 28a comprises first reagent 36 and a second strip 28b comprises second reagent 37. Alternatively, in some embodiments, a single strip 28 is configured to be used as both detector 24 and fluid identifier 26 and comprises both first and second reagents 36 and 37.

A hygienic pad 12 in accordance with additional embodiments of the present invention is depicted schematically in FIGS. 3A-3C. In this embodiment, a single reagent is used to detect the presence of amniotic fluid, meconium, and thick meconium. In this embodiment, first reagent 36 is preferably a reagent for detecting CEA, but may be other reagents capable of identifying amniotic fluid, meconium and thick meconium. Different thresholds of CEA may be set for each of these indications. In this embodiment, multiple test indicators 40 may be used along with a single control indicator 42.

In some embodiments, one or both of first and second reagents 36 and 37 may be present in collection body 11 from the beginning and in other embodiments may be added or partially added after collection body 11 has been contacted with the body fluid. In one embodiment, first reagent 36 is incorporated into collection body 11 while second reagent 37 is added or partially added during the process. In other embodiments, second reagent 37 is incorporated into collection body 11 while first reagent 36 is added or partially added during the process. Any combination of these options as well as additional reagents are included within the scope of the invention.

A single strip 28 or multiple strips 28 may be incorporated into hygienic pad 12. In some embodiments, as shown in FIG. 2B and in FIG. 3B, system 10 comprises a removable strip cover 31, which can be removed following contact with the fluid in order to read the results. System 10 is shown in FIG. 2C and FIG. 3C with strip cover 31 removed. Arrows indicate the flow direction of the fluid.

In some embodiments, as shown in FIG. 2C, a first strip 28a for CEA detection and a second strip 28b for AFP detection are positioned back-to-back within a hygienic pad 12. It should be readily apparent that the positioning of strips 28a, 28b is not limited to the positions shown herein and that any suitable position for one or multiple strips 28 within hygienic pad 12 is included within the scope of the invention. Front tips 30a, 30b of strips 28a, 28b contact one another within a central region of pad 12 within absorbent portion 21, and back tips 32a, 32b are located at opposite ends of pad 12 from each other, with one back tip 32a at or near first end 14 and the other back tip 32b at or near second end 16 of hygienic pad 12. Thus, fluid is absorbed by absorbent portion 21 of hygienic pad 12, and is carried by capillary action to both first end 14 and second end 16 of hygienic pad 12 via each of strips 28a, 28b.

A first test indicator 40a is a first T band 60, configured to appear when CEA is present in the fluid at above a predetermined threshold, and a second test indicator 40b is a second T band 62, configured to appear when AFP is present in the fluid at above a predetermined threshold. A first control indicator 42 is a first C band 64, configured to appear whether or not CEA is present in the fluid, and to indicate that the first test is valid, and a second control indicator 42 is a second C band 66, configured to appear whether or not AFP is present in the fluid and to indicate that the second test is valid. Only when full sample lateral flow has occurred, as determined by the appearance of both C bands 64 and 66, can the results be interpreted. If sample diffusion is too slow, a drop of detergent/"sample buffer" can be added to the absorbent portion 21. Table 1 summarizes the possible results and interpretations.

TABLE 1

| Interpretation | AFP | | CEA | |
| --- | --- | --- | --- | --- |
| | Band 60 T | Band 64 C | Band 62 T | Band 66 C |
| Full lateral flow has occurred (necessary for correct interpretation of the results) | – | + | – | + |
| Meconium-free amniotic fluid | + | + | – | + |
| Meconium stained amniotic fluid (MSAF) | + | + | + | + |

+, present; –, absent; T, test; C, control.

When only C bands appear, the sample fluid is not amniotic fluid; it can be urine due to urine leak/incontinence during pregnancy.

The use of both a meconium detector 24 and a fluid identifier 26, employing two different reactions, enhances the reliability of the system; false positive results, for example, are reduced. If the number of detectors and/or indicators is increased, it may make the system even sensitive and more specific.

In one embodiment of the present invention, reagent 36 is a substance which is used to detect the presence of CEA in the body fluid. Such reagents are known in the art and include, for example, antibodies that are used to screen for malignancies, such as colorectal, pulmonary, mammary, and gynecological. It has been found that a threshold for detecting CEA is indicative of the presence of meconium. The threshold may be in a range of 300 ng/µl to 700 ng/µl and in some embodiments, may be approximately 500 ng/µl. In other embodiments, reagent 36 may be a substance used to detect bile acids. Other substances which may be indicative of the presence of meconium may include, for example, steroids having alcohol and/or carboxyl groups, enzymes such as pancreatic enzymes, brush border enzymes, or transporters for glucose, alanine, or methionine. The present invention is not limited to these indicators of meconium and to the detecting reagents specific to each of those. Any suitable substance for detecting meconium is included within the scope of the present invention.

In one embodiment of the present invention, second reagent 37 is a substance which is used to identify the presence of alpha fetoprotein (AFP) in a body fluid. Such reagents are known in the art, such as, for example, antibodies for AFP. It has been shown that AFP detected at a threshold of at least 5 ng/µl is indicative of amniotic fluid. In other embodiments, as determined experimentally and presented in the EXAMPLES section, second reagent 37 may be CEA (with the same 5 ng/ml detection threshold). In other embodiments, fluid identifier 26 comprises an acid-base indicator. Since the pH of vaginal fluids is more acidic than the pH of amniotic fluid, it is possible to detect amniotic fluid based on pH. Thus, collection body 11 may be impregnated with an acid-base indicator, and the user may observe a color change in the presence of amniotic fluid. More specifically, the pH of amniotic fluid is generally between 7.0 and 7.5, and the pH of vaginal fluid without amniotic fluid is generally between 4.5 and 5.5. An alkaline pH, indicating a possible leakage of the amniotic fluid into the vagina, may be revealed in a method according to the invention by any acid-base indicator having a suitable pH range for its color change. Examples are bromocresol purple and nitrazine yellow. In some embodiments, in order to minimize false readings due to, for example, presence of blood or infections, fluid identifier 26 may alternatively or additionally be configured for detection of other components of amniotic fluid such as carbohydrates and/or proteins, such as glucose, fructose, prolactin, alpha-fetoprotein (AFP), and diamine oxidase.

In some embodiments, the reactions employed in collection body 11 for detecting materials typical of the amniotic fluid and/or meconium may comprise reaction cascades, in which a substrate present in the body fluid of the user is absorbed in the collection body and provides a product in a first reaction that reacts in another reaction, while providing an indicative color change. Additional reactions may also be involved in the cascade. The reactions employed in the color reactions or in reaction cascades may comprise, for example, enzymatic reactions. The reactions employed in the color reactions or in reaction cascades may comprise interactions with specific antibodies. Advantageously, stabilized or immobilized enzymes, which are sufficiently stable at room temperature or at body temperature for the time needed, may be employed.

In one embodiment, detecting reagent 36 for detecting components of meconium may comprise multiple reagents. For example, detecting reagent 36 may comprise one reagent for reacting with a component of the meconium, and a second reagent for providing a color or other indicator.

In one embodiment, one reagent of detecting reagent 36 is 3-α-HSD, another one of the reagents in detecting reagent 36 is NBT, and yet another reagent within detecting reagent 36 is diaphorase. In this embodiment, 3-α-HSD reacting with bile acids present in meconium produces NADH. NADH can then be visualized by reacting with NBT in the presence of diaphorase. In one embodiment, some or all of detecting reagents 36 are incorporated in collection body 11 during its manufacture. In another embodiment, some or all of detecting reagents 36 are added onto an absorbent portion 21 such as a patch on hygienic pad 12 only after absorbing the body fluid. Some of the reagents, such as enzyme solutions, may be stored in a refrigerator before use, and may be part of a kit for detecting meconium in the released amniotic fluid.

In one embodiment, absorbent portions 21 include collection members for collecting the body fluid therein before performing at least one of the reactions, wherein the reactions are performed outside of collection body 11.

In some embodiments, there is provided a kit for detection of at least one analyte present in a fluid, the kit comprising at least one collection body for collecting the fluid and at least one detector configured to detect presence of the at least one analyte in the fluid. The detector comprises a specimen sampling region for the fluid and a fluid-protective seal partially covering the detector, wherein only the specimen sampling region is uncovered by the fluid protective seal, and wherein the fluid protective seal comprises a material having acid resistance. The kit optionally further comprises printed instructions, such as a guide book, insert, instruction manual or the like.

Reference is now made to FIG. 4A, which is a schematic illustration of a kit 100 for prenatal detection of meconium in accordance with embodiments of the present invention. Kit 100 includes a collection body 11, which in the present embodiment is at least a portion of a multi-patch hygienic pad 112 comprising multiple patches 120, one or multiple reagents 36 to be used with at least one of multiple patches 120, and optionally a guide booklet 150. Patches 120 may comprise additional layers spatially stabilized within pad 112 supporting absorption or enabling localization of certain reagents. Materials known in the field, used as blotters or absorbers, acceptable for human use, are employed. Patches 120 may comprise layers separating reagents from direct contact with the user's body. In one embodiment, patches may have the form of test strips attached to the pad or within the pad structure, such as described above. In some embodiments, the outer layer of the pad may be torn off to enable better inspection of the color reagent after absorption of the body fluid. In some embodiments, patches 120 are not visible before using the pad, but their positions are denoted in the guide booklet 150 or manual.

In the embodiment shown herein, patches 120 include multiple detachable body fluid collection members 124. Collection member 124 may be, for example, a piece of material taken out of hygienic pad 112—for example, absorbent portion 21. The piece may be a preformed circle or other shape, for example, delimited with a weak line. In this embodiment, an external collection vial 125 may be used to place collection member 124 therein. Alternatively, collection member 124 may include a piece of absorbent material from pad 112 and a preformed structure, i.e. collection vial, incorporated into the pad; such structure may be, for example, a plastic cylindrical body open on one or both ends. In either case, collection member 124 is designed to be removed from pad 112 and analyzed outside of pad 112 using other portions of kit 100.

Kit 100 further includes a detection device 134, which may be for example, a prepared test tube, vial or reaction bottle. An example of a detection device 134 is shown as a vial 136 in FIGS. 4A and 4B. In the embodiment shown herein, vial 136 includes a removable cap 138. Vial 136 further includes therein one or multiple detecting reagents 36 and/or identifying reagents 37. Reagents may be separated from one another by one or multiple partitions 140. Collection member 124 is introduced into vial 136 and thus brought into contact with detecting reagents 36 and/or identifying reagents 37. In vial 136, a visible color change indicates probable presence of components usually found in meconium or amniotic fluid, such as bile acids or CEA. In one example, vial 136 includes reagents 3-α-HSD, NBT, and diaphorase, which provide a color ranging from dark red to brown to black with bile acids.

In some embodiments, pad 112 includes an area with a pH sensitive surface that changes color when exposed to a relatively basic environment, indicating probable presence of the amniotic fluid; such an area may be on a surface of pad 112 or may be in one of patches 120, for example.

Kit 100 includes simple steps that can be easily performed at home by a lay person. Steps of a method of using kit 100 are now described. First, a pregnant subject continuously wears hygienic pad 112 ready to collect body fluid, eventually comprising escaped amniotic fluid, throughout the pregnancy term. The subject has detection device 134 (such as vial 136) with reagents therein. When body fluid is absorbed into pad 112, the subject removes the pad, and separates collection member 124 from pad 112. Cap 138 of vial 136 is removed, and collection member 124 is placed therein. Cap 138 is replaced onto vial 136. In embodiments of the present invention, replacing cap 138 results in breaking of partitions 140 located over a strainer 141 and subsequent mixing of reagents with the body fluids. For example, collection member 124, such as a blotter soaked with the body fluid, is placed onto a portion of vial having cap 138, and is then inserted into vial 136 while breaking partitions 140, thereby mixing reagents and the sample. If using, for example, the reaction system comprising 3-α HSD/NBT/diaphorase, the initial reaction color is yellow; when meconium is present the color changes to dark red/brown or black.

Reactions of the present invention may be performed in situ in the pad after addition of reagents, or in vitro after removing collection member 124 and transferring it to detection device 134. Detection device 134 may be provided as a separate item in kit 100 according to the invention, or it may be attached on or within pad 112, being prepared for later reaction, including active steps to be taken by the user of kit 100, for example further mixing of reagents with the body fluids.

In one embodiment, collection member 124 includes absorbent material which is configured to increase the sorption of desired components from body fluids, such as bile acids, thereby eventually concentrating the components to be detected in collection member 124; said configuring may comprise special structural micro-arrangement of the sorbent, or inclusion of a highly sorbing blotter, or impregnation with a chemical that increases sorption of said desired component based, for example. The member is configured so that maximal sorption of required components occurs, while minimizing the contact of reagents with the skin. As schematically shown in FIG. 4B, sample S, entrapped in collection member 124 and connected to cap 138, is inserted into the opened detection device 134. Partitions 140 separating the reagents ($R_1$ and $R_2$) are broken as collection member 124 inside collection vial 125 moves down towards vial 136. The absorbent material with body liquid within collection member 124 may be squeezed over a strainer 141 placed below partition 140 to release the liquid from the fibers, thereby mixing the reagents with the sample, and starting the color reaction to be visually checked. Vial 136 may be at least partially transparent.

The system of the present invention can be easily employed by lay people at home. In some embodiments system 100 can be modified for the use with assays described in system 10. In some embodiments, the invention can be modified for the use of skilled medical personnel and utilized for additional testing. In some embodiments, system 10 comprises a probe such as a cylindrical probe insertable into the vagina (similar to a tampon) or by an applicator. In some embodiments, system 10 may be used as a 'bedside test' and may assist the skilled/medical personnel in evaluating fetal distress and the associated etiologies.

In some embodiments, the system of the present invention is useful for detecting an analyte in a non-body fluid, such as, for example in seawater. For example, old mines in seawater that may drift from one location to the other carry a risk to civilian and military ships. The detection of dissolved explosives can indicate the proximity of an old underwater mine. For example, old underwater mines release explosive molecules such as 2,4,6-trinitrotoluene (TNT). The sampling of seawater, in various depths, with the system disclosed herein for TNT can assist in the localization of the old mine. The system of the present invention can be fully submerged in seawater and retain its functionality.

EXAMPLES

Example 1: Detection of CEA and/or AFP

After obtaining informed consent, amniotic fluid specimens is collected from women in labor following rupture of membranes. Urine specimens are collected through a urethral catheter from time to time during and after labor.

Phase I of this experiment is performed in order to determine whether detectable levels of CEA and/or AFP may be found and whether these levels may have diagnostic value. Phase I is performed as follows: Amniotic fluid specimens are examined by medical personnel and classified as clear amniotic fluid or meconium stained amniotic fluid (MSAF). Samples of clear amniotic fluid and samples of MSAF are then tested using the assay system disclosed herein.

The results show that CEA levels are significantly higher in MSAF than in clear amniotic fluid, and that CEA levels are normal in urine of women with MSAF.
1. In order to differentiate MSAF from clear amniotic fluid, the assay should have sensitivity threshold of around 500±100 ng/ml. Furthermore, the sensitivity threshold for heavy meconium can be determined at around 1000±200 ng/ml. Amniotic fluid AFP levels are not affected by meconium secretion.
1. Even in women with MSAF, urine CEA and AFP levels are in a normal range. Thus, through the measurement of CEA and/or AFP levels, involuntary urine secretion can be differentiated form clear amniotic fluid secretion or MSAF secretion.

AF CEA concentration is likely directly related to meconium concentration. Even in urine of women with MSAF, CEA concentrations are within normal physiological limits. Therefore, CEA can serve both as an amniotic fluid marker and a MSAF marker as well as a thick MSAF marker. In order to do so, thresholds of 5 ng/ml; 500 ng/ml and 1000 ng/ml are shown to be effective for determining rupture of membranes (ROM), MSAF, and thick MSAF, respectively. The collection body 11 as shown in the embodiment of FIGS. 3A-3C may thus be comprised of a CEA detection agent with thresholds comparable or similar to the ones described herein.

Phase II of the experiment is then conducted to determine whether commercial assays available on the market for detection of cancer markers can be used for meconium detection in accordance with the present invention. Three potential problems have been identified:

Normal serum/plasma levels of CEA are up to 5 ng/ml. Commercial assays are designed to detect CEA levels of 4-5 ng/ml and higher (detection threshold of 4-5 ng/ml) for the screening or follow-up of several malignancies. The commercial assays are designed for serum or plasma specimens rather than for amniotic fluid specimens. Usually, serum has lower viscosity than amniotic fluid. Amniotic fluid expelled out from the uterus may contain heavy secretions (such as Vernix, mucus, and blood) and may have higher viscosity than serum or plasma. In order for the assay to be useful in the present invention, it would need to have independent ability to filter out these heavy secretions and do the sampling without the aid of any preceding manual procedure(s). The commercial assays function under dry conditions only. The assay of the present invention must function under highly moist conditions, and at acidic pH. The assay's reagents and antibodies must somehow be isolated and protected from normal vaginal secretions and must be configured to react only upon rupture of membranes i.e., water breaking).

Phase II is conducted using the system as disclosed herein.

Phase III of this experiment involves testing a prototype. The partially sealed modified CEA immunoassays as disclosed herein are built into custom designed pads (pantyliners, hygienic napkins etc.) that include heavy secretion filters. These pads are exposed to 100% air humidity conditions at pH 4 for 12 hours or are worn by female volunteers for up to 12 hours. Following these two exposures, the pads are inspected. After this time period, it is found that the reagents and antibodies remain protected and no lateral flow diffusion/reaction occurs. Afterwards, clear amniotic fluid or MSAF specimens are applied to the pads.

Results obtained are expected to be comparable to results obtained in Phase II of this experiment.

A pad or other collection body comprising these two assays has the following advantages: (1) Blood does not interfere with meconium detection by CEA and, therefore, light/heavy meconium masked by significant blood secretions can be identified. (2) Because AFP and CEA are not excreted into urine, the frequent dilemma of ROM vs. urinary incontinence in pregnant women can be easily solved: samples will be positive to AFP only or to AFP+CEA when ROM has occurred. Samples will be negative to AFP and to CEA if urine leak has occurred. According to U.S. Pat. No. 5,514,598, the 14 kilodalton protein (a proposed meconium marker) is present in urine and therefore cannot help with solving the dilemma above. Moreover, in comparison with CEA, the 14 kilodalton protein assay is less sensitive and specific for meconium. (3) Frequent sampling of amniotic fluid after ROM has occurred can reveal the time point of transition from meconium-free amniotic fluid to MSAF. This information can reveal the onset of fetal distress and necessitate exigent medical intervention (intrauterine resuscitation procedures, caesarean section, etc.).

Example 2: Detection of Amniotic Fluid and MSAF

A system as disclosed herein was used for detection of deoxycholic acid (DOC, a bile salt). DOC was purchased from Sigma-Aldrich (St. Louis, Mo., USA). DOC was applied to the solution containing the reconstituted kit reagents at room temperature. The original solution color is yellow. The presence of DOC initiated a two-stage reaction that led to a color change to dark red/brown after ten minutes. The presence of low DOC concentrations could be easily detected by the naked eye. Controls containing distilled water did not lead to any color change. Solutions maintained a stable color for approximately one hour. Meconium bile acids can be detected by the color change. A pH sensitive pad for the detection of amniotic fluid (Common-Sense Inc., Caesarea, Israel) can be combined with bile acid detection method.

Example 3: A Platform for Identifying Etiologies of Fetal Distress After ROM Occurs High amniotic glucose level can be a result of uncontrolled gestational diabetes, which is a possible etiology for fetal distress. A colorimetric assay for glucose can be done by coupling the activities of the two enzymes: glucose oxidase and glucose peroxidase. In the first step, glucose oxidase catalyzes the reaction: glucose+oxygen gluconolactone+hydrogen peroxide. In the second step, the hydrogen peroxide is used by the peroxidase to convert a chemical substrate (called a chromogen) from an uncolored form to a colored one. This reaction is used in commercial urinalysis kits. For example: the enzymes and the chromogen can be attached to the stick. When glucose is present, the reactions described above take place, and the stick changes color. In cases of early preterm premature rapture of membranes (PPROM; <32nd gestational week), the chances of placental abruption are as high as 10-15%. Benign abruption can last for days or weeks with mild maternal bleeding. However, placental abruption can be dynamic and exacerbate into significant maternal/fetal bleeding, and can be accompanied by fetal distress and meconium secretion. PPROM accruing before the 34th gestational week is usually managed by close in-hospital expectant monitoring and attempts to avoid delivery. The rationale is to minimize early prematurity complications. However, exacerbation of placental abruption may lead to severe fetal distress and the need for an emergent cesarean section delivery. The occurrence of severe placental abruption can be identified by the appearance of MSAF together with fetal hemoglobin. Therefore, colorimetric assays for fetal hemoglobin and for CEA can help with the early diagnosis of placental abruption exacerbation.

In an attempt to identify the underlying cause of fetal distress, colorimetric assays for glucose, and maternal and fetal hemoglobin can be incorporated into the method according to the invention.

Example 4: Detection of Embryonic/Fetal Tissue

AFP is produced by the embryo and circulates in its blood. AFP concentration in the embryo's serum is significantly higher in the in the maternal serum throughout the whole pregnancy. A measurement of a high level of AFP the in the vaginal secretions can indicate a passage of embryonic tissue out of the uterus (e.g., embryonic bleeding). A lateral flow immunoassay for AFP, embedded in a pad, can serve as a bedside detector for the presence of embryonic components in vaginal secretions. On the other hand, embryonic tissue is absent in a complete molar pregnancy and therefore, in this case AFP level in the contents evacuated from the uterus would be very low and similar to its level in the maternal serum.

AFP testing was carried out using the system as disclosed herein, substantially as described in Example 1.

Example 5: Resistance to Acid 17-micron nylon and polyethylene and 0.1 mm flexible glass films were exposed to various concentrations of carbonic acid (pH of 3.5 to 6). The time taken (in seconds) to film transparency loss; visualized leakage of fluid through the film; and. visualized break down of the film (loss of integrity) was determined at pH values 3.5, 4, 4.5, 5, 5.5 and 6. Film transparency loss was defined according to the following: Two parallel solid black lines were printed on a white paper sheet. The lines were 10 mm long, 1 mm thick, and 2 mm apart from each other. The tested film was placed over the sheet with the printed lines. Loss of transparency was defined as the point at which a normal human eye would be unable to distinguish between the two black lines.

Figure 5:
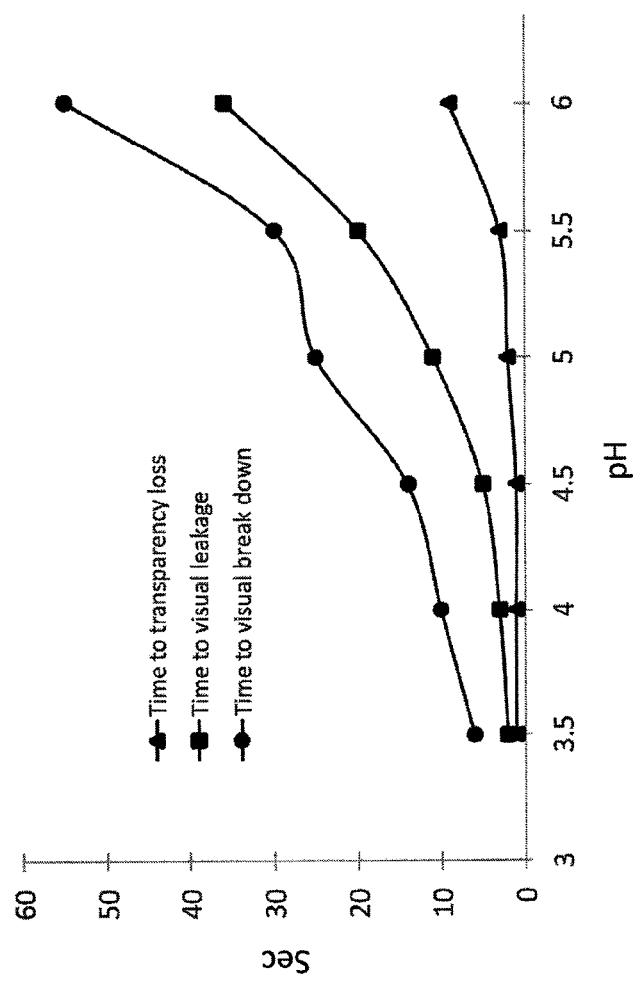
FIG. 5 is a line graph showing the loss of integrity of nylon on exposure to acid.

With regard to nylon, on exposure to a stronger acidic environment (lower pH), loss of integrity was achieved at an earlier time (FIG. 5). By contrast, the polyethylene and glass exposure to the various acidic environments did not result in transparency loss, fluid leakage, or break down of its structure (i.e., loss of integrity) for up to 5 minutes.

It was concluded that a weak acid such as carbonic acid attacks and leads to integrity loss of nylon whereas polyethylene and glass seem to be resistant to carbonic acid attack (i.e., acid resistant).

Example 6: A Lateral Flow Assay Submerged in Whole Blood and Capable of Detecting a Dissolved Analyte The capillary action of whole blood masks the colored test and control lines (indicator lines) formed on a lateral flow assay strip. Whole blood contains plasma and cellular components. When an analyte of interest is dissolved in the plasma, the plasma and the cellular components should be separated from each other and the sample testing should be done, preferably, on the plasma component only. In this way the marked red pigment of the red blood cells (RBCs) in the cellular component will not mask the lateral flow assay's indicator lines. It is known in the art that the usage of filters with pores smaller than the diameter of red blood cells (RBCs), with or without making the RBCs less flexible (U.S. Pat. No. 8,535,617), can decrease the entry of RBCs into the detection region of the lateral flow assay strip. However, these filters also prevent other larger circulating cells, such as white blood cells (WBCs) and potentially malignant WBCs from entering the detection region. Therefore, a lateral flow assay designed to detect malignant WBCs would have to include a means for binding or trapping RBCs rather than a filter for RBCs. One way to achieve this is by providing a sampling region comprising an absorbent material that binds platelets and leads to their activation. The activation of platelets leads to the formation of a clot that traps RBCs and therefore, assists with their separation from the rest of the sample.

A system as disclosed herein was provided, wherein the specimen sampling region comprised an absorbent material made of oxidized non-regenerated cellulose (a material known in the art to activate platelets). The system was fully submerged in a 6 mL non-clotted whole blood specimen from a pregnant woman (normally containing high concentration of AFP). The system was removed and visually inspected. A blood clot was visualized at the sampling area within 2 minutes and the test and control lines were clearly visualized by 5 minutes. The conclusion from this experiment was that binding and activation of platelets at the the sampling region enables trapping of RBCs and the subsequent visualization of the test and control lines. In alternative embodiments, a specimen sampling region comprises an absorbent embedded with a pro-clotting material—such as kaolin (a mineral known in the art to accelerate the natural clotting ability of blood) or a specimen sampling region is impregnated with fixed antibodies specific for RBCs. Lewis et al. [1] showed the minimal time to clot formation with oxidized non-regenerated cellulose was 50-100 sec. Therefore, an absorbent material that triggers platelet activation within 50 seconds would be considered as pro-clotting absorbent.

U.S. Pat. No. 6,309,887 discloses a method for detecting an analyte in the cellular component of a whole blood specimen. This patent describes an absorbent material impregnated with an anticoagulant that prevents clot formation and allows a capillary action of the whole blood sample. However, U.S. Pat. No. 6,309,887 neither shows a method of separating RBCs from the sample absorbed nor a solution to overcome the masking of the red pigment. On the other hand, penetration of plasma with activated coagulation factors into the detection zone (with or without RBCs) may interfere with the assay's functionality.

Figure 6:
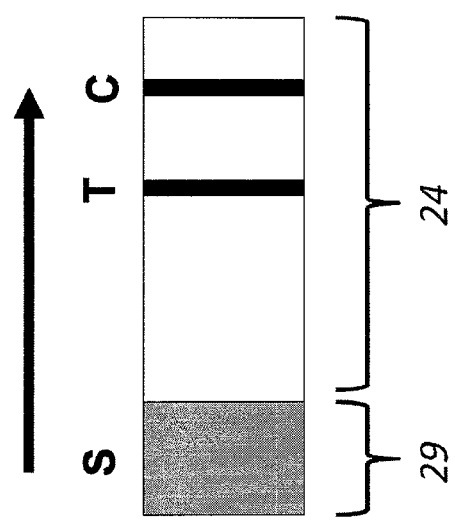
FIG. 6 is a schematic representation of a lateral flow immunoassay with pro-clotting and anti-clotting properties.

According to some embodiments, the system of the present invention, sampling region 29 and detection region 24 comprise materials with pro-clotting (e.g., oxidized cellulose) and with anti-clotting (e.g. paper embedded with citrate), properties, respectively (FIG. 6). The modification of a detection region embedded with citrate did not change the observed results described above: a blood clot was visualized at the sampling area within 2 minutes and the test and control lines were clearly visualized by 5 minutes.

While this invention has been described in terms of some specific examples, many modifications and variations are possible. It is therefore understood that within the scope of the appended claims, the invention may be realized other than as specifically described. For example: immunochromatographic assays for squamous epithelium carcinoma associated Antigen (SCCA, WO2010150804), placental alpha-microglobulin-1 (PAMG-1; Phupong and Sonthirathi, 2012), CA-125 tumor marker, or AFP with Insulin-like growth factor binding protein-1 (IGFBP-1; WO2011151597) can replace AFP for the detection of ROM. The same applies for other materials (molecules, proteins, gut enzymes, bilirubin byproducts, intestinal wall plasmatic membrane transporters, etc.) that can replace bile acids or CEA for the detection of meconium.

What is claimed is:

1. A system for detection of at least one analyte present in a fluid, the system comprising:
    a detector configured to detect presence of the at least one analyte in the fluid, said detector comprising a specimen sampling region for said fluid; and
    a fluid protective seal positioned such that only said specimen sampling region is uncovered by said fluid protective seal,
    wherein said fluid protective seal comprises a material having acid resistance to an acid solution of pH 3.5 to 6,
    wherein said acid resistance to said acid solution of pH 3.5 to 6 comprises at least one property selected from the group consisting of resistance to loss of transparency for at least 30 seconds upon full immersion in said acid solution of pH 3.5 to 6; resistance to passage of fluid for at least 30 seconds upon full immersion in said acid solution of pH 3.5 to 6; and retention of physical integrity for at least 30 seconds upon full immersion in said acid solution of pH 3.5 to 6.

2. The system of claim 1, wherein said detector comprises a lateral flow assay.

3. The system of claim 1, wherein said detector comprises an immunoassay.

4. The system of claim 1, wherein said specimen sampling region is configured to bind platelets within 50 seconds.

5. The system of claim 4, wherein said specimen sampling region comprises a material selected from the group consisting of oxidized cellulose, absorbent material with glass fragments and absorbent material with kaolin.

6. The system of claim 3, wherein said immunoassay comprises a lateral flow immunochromatographic assay.

7. The system of claim 3, wherein said immunoassay comprises an immunoassay strip.

8. The system of claim 7, wherein said immunoassay strip comprises a front tip, a back tip, an upper body portion and a lower body portion extending between said front tip and said back tip, wherein said specimen sampling region comprises said front tip of said strip, each of said front tip, back tip upper body portion and lower body portion comprising an outer surface, wherein said fluid-protective seal is positioned on said outer surface of said upper body portion, said lower body portion and said back tip such that only said front tip is uncovered by said fluid protective seal, such that said fluid comes into contact with said front tip and is carried along said body portion to said back tip.

9. The system of claim 8, wherein said immunoassay strip comprises a first antibody for reacting with said at least one analyte of said fluid, wherein said antibody is positioned at said front tip of said strip.

10. The system of claim 1, further comprising a fluid identifier comprising a reagent for reacting with said fluid, wherein said reagent is configured to identify said fluid.

11. The system of claim 1, wherein said fluid comprises a biological fluid released from the body of a subject.

12. The system of claim 11, wherein said biological fluid is selected from the group consisting of amniotic fluid, urine, saliva, sweat, vaginal discharge, semen and blood.

13. The system of claim 12, wherein said biological fluid is amniotic fluid and wherein said detector comprises a detector for the presence of at least one analyte of amniotic fluid selected from the group consisting of a carbohydrate and a protein.

14. The system of claim 13, wherein said protein is selected from the group consisting of alpha-fetoprotein (AFP), carcino-embryonic antigen (CEA), epithelium carcinoma associated Antigen (SCCA), placental alpha-microglobulin-1 (PAMG-1), CA-125 tumor marker, Insulin-like growth factor binding protein-1 (IGFBP-1), Prostate serum antigen (PSA) and diamine oxidase.

15. The system of claim 14, wherein said protein comprises AFP, wherein said detector for presence of AFP is configured to detect an amount of AFP in said biological fluid, and wherein a presence of amniotic fluid is indicated when said detected amount of AFP is above a pre-determined threshold.

16. The system of claim 15, wherein said pre-determined threshold is approximately 10 ng/ml.

17. The system of claim 14, wherein said protein comprises CEA, wherein said detector for presence of CEA is configured to detect an amount of CEA in said biological fluid, and wherein a presence of amniotic fluid is indicated when said detected amount of CEA is above a pre-determined threshold.

18. The system of claim 17, wherein said pre-determined threshold is at least 5 ng/ml.

19. The system of claim 1, further comprising a collection body for collecting said biological fluid.

20. The system of claim 19, wherein said collection body comprises at least a portion of a hygienic pad, an underwear or a tampon.

21. The system of claim 1, wherein said fluid comprises a non-biological fluid.

22. The system of claim 21, wherein said fluid comprises a liquid selected from the group consisting of sea water, rainwater, river water, lake water, reservoir water, well water, a source of drinking water, and sewage.

23. The system of claim 21, wherein said detector comprises a detector for the presence of an analyte selected from the group consisting of 2,4,6-trinitrotoluene, asbestos, benzene, aflatoxins, ricin, cholera toxin, prion, pertussis toxin, ectatomin, conopeptides, abrin, verotoxin, tetanospasmin, botulinum toxin, DNA and RNA.

24. The system of claim 19, wherein said detector is located externally to said collection body.

25. The system of claim 24, wherein at least a portion of said collection body is detachable, wherein said detector is configured to detect presence of the at least one analyte in the fluid collected in said detachable portion of said collection body.

26. A kit for detection of at least one analyte present in a fluid, the kit comprising:
at least one detector configured to detect presence of the at least one analyte in the fluid, said at least one detector comprising a specimen sampling region for said fluid and a fluid protective seal positioned such that only said specimen sampling region is uncovered by said fluid protective seal, wherein said fluid protective seal comprises a material having acid resistance, to an acid solution of pH 3.5 to 6,
wherein said acid resistance to said acid solution of pH 3.5 to 6 comprises at least one property selected from the group consisting of resistance to loss of transparency for at least 30 seconds upon full immersion in said acid solution of pH 3.5 to 6; resistance to passage of fluid for at least 30 seconds upon full immersion in said acid solution of pH 3.5 to 6; and retention of physical integrity for at least 30 seconds upon full immersion in said acid solution of pH 3.5 to 6; and
at least one collection body for collecting said fluid.

27. A method of detecting at least one analyte present in a fluid, the method comprising:
providing a detector configured to detect presence of the at least one analyte in the fluid, said detector comprising a specimen sampling region for said fluid and a fluid protective seal positioned such that only said specimen sampling region is uncovered by said fluid protective seal, wherein said fluid protective seal comprises a material having acid resistance, to an acid solution of pH 3.5 to 6,
wherein said acid resistance to said acid solution of pH 3.5 to 6 comprises at least one property selected from the group consisting of resistance to loss of transparency for at least 30 seconds upon full immersion in said acid solution of pH 3.5 to 6;
resistance to passage of fluid for at least 30 seconds upon full immersion in said acid solution of pH 3.5 to 6; and retention of physical integrity for at least 30 seconds upon full immersion in said acid solution of pH 3.5 to 6; collecting said fluid; and
contacting said fluid with said specimen sampling region of said detector.

* * * * *